(12) United States Patent
Versteeg et al.

(10) Patent No.: US 9,000,230 B2
(45) Date of Patent: Apr. 7, 2015

(54) METHOD OF PREPARING GLYCEROL ALKYL ETHERS

(75) Inventors: Geert F. Versteeg, Enschede (NL); Piet Ijben, Enschede (NL); Wouter Nicolaas Wermink, Enschede (NL); Katarína Klepáčová, Enschede (NL); Sjaak Van Loo, Enschede (NL); Wladimir Kesber, Enschede (NL)

(73) Assignee: The GTBE Company N.V., Enschede (NL)

( * ) Notice: Subject to any disclaimer, the term of this patent is extended or adjusted under 35 U.S.C. 154(b) by 637 days.

(21) Appl. No.: 12/990,241

(22) PCT Filed: Apr. 30, 2009

(86) PCT No.: PCT/IB2009/006929
§ 371 (c)(1),
(2), (4) Date: Jan. 10, 2011

(87) PCT Pub. No.: WO2009/147541
PCT Pub. Date: Dec. 10, 2009

(65) Prior Publication Data
US 2011/0098510 A1    Apr. 28, 2011

(30) Foreign Application Priority Data
Apr. 30, 2008    (ZA) .................................. 2008/03745

(51) Int. Cl.
*C07C 41/06*    (2006.01)

(52) U.S. Cl.
CPC ........... *C07C 41/06* (2013.01); *C07C 2527/054* (2013.01)

(58) Field of Classification Search
USPC ......................................... 568/697, 679, 680
See application file for complete search history.

(56) References Cited

U.S. PATENT DOCUMENTS

| | | | |
|---|---|---|---|
| 1,968,033 | A | 7/1934 | Evans et al. |
| 2,255,916 | A | 9/1941 | Doelling |
| 5,308,365 | A | 5/1994 | Kesling, Jr. et al. |
| 5,476,971 | A | 12/1995 | Gupta |
| 5,578,090 | A | 11/1996 | Bradin |
| 6,015,440 | A | 1/2000 | Noureddini |
| 2007/0238905 | A1 | 10/2007 | Arredondo et al. |
| 2007/0283619 | A1 | 12/2007 | Hillion et al. |

FOREIGN PATENT DOCUMENTS

WO    2007061903 A1    5/2007

*Primary Examiner* — Rosalynd Keys
(74) *Attorney, Agent, or Firm* — The Webb Law Firm

(57) ABSTRACT

A process for glycerol etherification, including a recycle of glycerol and/or mono-ether, to produce glycerol alkyl ethers with low amount of mono-ether by reacting glycerol and olefinic hydrocarbon, and/or the corresponding aldehydes, ketones and alcohols, having 2 to 10 carbon atoms in the presence of homogeneous acid catalyst with hindered formation of olefin oligomers comprising of two essential steps: reaction step (1) neutralization and salt removal step (2).

20 Claims, 1 Drawing Sheet

METHOD OF PREPARING GLYCEROL ALKYL ETHERS

BACKGROUND OF THE INVENTION

1. Field of the Invention

This invention relates to an advanced process for producing glycerol alkyl ethers with low amount of mono-alkyl ether by reacting glycerol and straight, branched or cyclic olefinic hydrocarbons, and/or the corresponding aldehydes, ketones and alcohols, in the presence of a homogeneous acid catalyst which enables the production of glycerol ethers free from by-products formed by olefin oligomerization.

2. Description of the Related Art

In recent years environmental restrictions suggested the application of biofuels as transportation fuel. Biodiesel has been implemented in many countries as a compulsory component of traditional oil based diesel fuel and the production of biodiesel from renewable sources is increasing rapidly. In the biodiesel process, besides biodiesel, derived from natural oils and fats by transesterification with lower alcohols as methanol or ethanol, also roughly 10% of glycerol in the form of a (watery) solution is produced as a by-product. The increase in biodiesel production resulted in an excess of glycerol on the chemical market and disturbed world market glycerol prices. One of the possible solutions for glycerol overproduction is the transformation into glycerol alkyl ethers, particularly into glycerol tert-butyl ethers which are exploitable as a diesel and biodiesel fuel additive.

The preparation of alkyl ethers of glycerol is a known reaction. Alkyl ethers of glycerol can be formed by the Williamson's synthesis (See U.S. Pat. No. 2,255,916) when alcoxide is added to a suitable alkyl halide to form the ether, or can be formed by the reaction of alcohol or olefin in the presence of an acid catalyst. Many patents concerning the glycerol alkyl ethers production via the etherification reaction of glycerol and olefin have been published. One of the first patents applied in this field is U.S. Pat. No. 1,968,033 (published in 1934) describing the tertiary ether formation from glycerol and isobutylene with the aid of sulfuric acid as homogeneous catalyst.

In general, the procedure is carried out by reacting glycerol and isobutylene using an acid catalyst. As described in patent U.S. Pat. No. 5,476,971 one of the methods for producing ditertiary butyl ether of glycerol is the reaction of glycerol and isobutylene in a two phase reaction system. The reaction mixture is phase separated into a heavier glycerol and catalyst containing polar phase and a lighter hydrocarbon phase from which product ethers can be readily separated. As a homogeneous catalyst, p-toluenesulfonic or methanesulfonic acid was used. Another conventional process (US 2007/0238905 A1) describes the process for converting glycerol to alkyl glycerol ethers from glycerol, alkyl alcohol and an etherification catalyst to obtain a reaction product comprising of alkyl glycerol ethers.

The alkyl ethers of glycerol are excellent oxygen additives for diesel and biodiesel fuel. The di- and tri-alkyl ethers show good miscibility with commercial diesel fuel and thus can be used in the concentrations required for the desired emissions reduction. As stated in U.S. Pat. No. 6,015,440 glycerol tert-butyl ethers added to biodiesel fuel proved the decrease in cloud-point and improved viscosity properties of biodiesel fuel mixed with glycerol tert-butyl ethers. According to patent U.S. Pat. No. 5,308,365 the use of ether derivatives of glycerol which, when incorporated in standard 30-40% aromatic containing diesel fuel, provides reduced emissions of particulate matter, hydrocarbons, carbon monoxide and unregulated aldehyde emission. The international application WO 2007/061903 A1 relates to compositions which include an alcohol and mixture of glycerol ethers, potentially derived from renewable sources. When combined with gasoline/ethanol blends, the glycerol ethers can reduce the vapour pressure of ethanol and increasing the fuel economy. When added to diesel fuel/alcohol blends, glycerol ethers improve the cetane value of the blends. Patent U.S. Pat. No. 5,578,090 describes a fuel additive composition including fatty acid alkyl esters and glyceryl ethers prepared by etherifying glycerol with one or more olefins in the presence of acid catalyst. Utilization of crude glycerol from the transesterification process is stated in patent US 2007/0283619 A1. In the transesterification process a heterogeneous catalyst was applied. The glycerol by-product from this process is free from catalyst and is at least 98% pure. It contains no metals, no neutralization salts and no additional purification is required. The glycerol obtained may be used directly in an etherification reaction with isobutylene in the presence of an acid catalyst.

Various typical properties of cited patent applications are listed below:

U.S. Pat. No. 2,255,916 by Doelling relates to the ethers of glycerol produced by Williamson's synthesis.

U.S. Pat. No. 1,968,033 by Evans teaches the reaction for preparing tertiary ethers of glycerol by using glycerol and isobutylene in the presence of sulfuric acid.

U.S. Pat. No. 5,476,971 by Gupta describes the process for preparation of ditertiary butyl ether preparation in the two separate liquid phases comprised from glycerol and isobutylene using homogeneous catalyst.

US 2007/0238905 by Arredondo patents the way of producing alkyl glycerol ethers by reacting glycerol with correspondent alkyl alcohol.

U.S. Pat. No. 6,015,440 by Noureddini concerns about the improved biodiesel composition comprised of methyl esters and glycerol ethers produced from the purified glycerol by-product formed in the transesterification process.

U.S. Pat. No. 5,308,365 by Kesling describes the positive influence of dialkyl and trialkyl derivatives of glycerol on particulate matter emissions when incorporated in conventional diesel fuel.

WO 2007/061903 by Bradin relates to compositions which include a mixture of glycerol ethers, which when combined with gasoline/ethanol blends, can reduce the vapour pressure of the ethanol.

U.S. Pat. No. 5,578,090 by Bradin deals with the fuel composition that includes fatty acids alkyl esters and glyceryl ethers, prepared by etherifying glycerol with one or more olefins in the presence of acid catalyst.

US 2007/0283619 by Hill provides a process where non-treated glycerol by-product (from triglycerides transformation) is reacted with an olefinic hydrocarbon to form glycerol ethers.

SUMMARY OF THE INVENTION

The process of production of glycerol alkyl ethers by reaction of glycerol with straight, branched or cyclic olefinic hydrocarbons, and/or the corresponding aldehydes, ketones and alcohols, having from 2 to 10 carbon atoms in the presence of homogeneous acid catalyst is disclosed. According to the invention the first and the most important part of the reaction with olefin, preferably isobutylene is carried out in the polar glycerol phase of a multi phase system. Homogeneous acid catalyst as p-toluenesulfonic acid, methanesulfonic acid, but preferably sulfuric acid due to its low price, is dissolved in the polar glycerol phase where the etherification reaction occurs. The solubility of olefinic hydrocarbon in this phase is too low to form olefin dimers. As the reaction proceeds the concentrations of reaction products increase, and the amount of olefin phase decreases. In this for the olefin oligomerization less critical part of the etherification reaction one reaction phase is formed. The process comprises of two sequential and essential steps: 1) etherification step where the glycerol is reacted by homogeneous catalysis with an olefin selected from olefins, and/or the corresponding aldehydes, ketones and alcohols, containing 2-10 carbon atoms in a polar glycerol phase, where the oligomerization of olefins is eliminated because of insufficient catalyst concentration in the olefinic hydrocarbon phase; 2) neutralization step where the acid catalyst is neutralized with caustic and the formed salt is separated with an appropriate separation method. Besides neutralizing the catalyst, this step is the outlet of salts. In case salts are present in the feed glycerol, this step, via the salt outlet, prevents the build-up of salts caused by the high boiling components recycle. Optionally additional unit operations may be integrated to the process but are not necessary, for instance: a distillation unit where low boiling components, glycerol and mono-alkyl ether can be separated from the product of di- and tri-alkyl ether; etc.

DETAILED DESCRIPTION OF THE PREFERRED EMBODIMENTS

Figure 1:
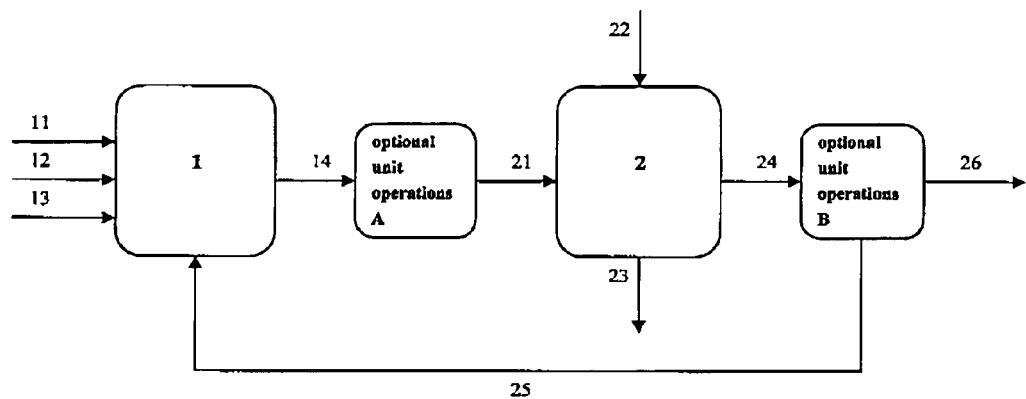
FIG. 1 is a schematic view of a process for production of glycerol alkyl ethers according to the principles of the present invention.

In accordance with the present invention a process for production of glycerol alkyl ethers with a low amount of mono-ethers and free from by-products formed by the olefin oligomerization catalyzed with homogeneous catalyst is disclosed. Referring to FIG. 1, there is shown an embodiment of a process describing an etherification reaction conducted in the etherification reactor 1 which may include for example a batch or continuously operating reactor. FIG. 1 shows that feed streams comprise the glycerol 11; olefin 12, preferably isobutylene and homogeneous catalyst 13, preferably sulfuric acid. The recycled stream 25 from additional unit operations may be led into the first reaction step together with the feed components. Said feed stream glycerol can be obtained by any method, but preferably treated or untreated glycerol from a transesterification process can be used. The term "olefin" refers to unsaturated straight, branched or cyclic hydrocarbon, and/or the corresponding aldehydes, ketones and alcohols, containing 2 to 10 carbon atoms, but preferably ethylene, propylene and/or isobutylene, and/or the corresponding aldehydes, ketones and alcohols. The mole ratio of olefinic hydrocarbon, and/or the corresponding aldehydes, ketones and alcohols, and glycerol is at least 0.1:1 and can be as high as 10:1, but preferably 2:1 where the yield of desirable glycerol di-alkyl ether is the highest. In the following part of the description only olefins is used as possible feed. The first and for the olefinic oligomerization reaction also the most critical period of the reaction operates in a two phase system. The bottom polar glycerol phase comprises of mainly glycerol and the acid homogeneous catalyst, the top non-polar hydrocarbon phase consists mainly of olefin, preferably ethylene, propylene and/or isobutylene. The homogeneous catalyst, predominantly dissolved in the polar phase, avoids formation of olefin dimers because of the low solubility of olefinic hydrocarbon in the polar glycerol phase and the reaction between glycerol and olefin is more feasible than the reaction between two molecules of olefin. Moreover, the homogeneous catalyst is almost insoluble in the non polar olefin phase and therefore oligomerization of the olefin is minimized. The catalyst can be homogeneous acid catalyst such as p-toluenesulfonic acid, methanesulfonic acid, but preferably inexpensive sulfuric acid which does not have to be recycled.

As the reaction proceeds, the concentration of glycerol alkyl ethers in the glycerol phase increases what results in lower polarity and higher solubility of olefin in this phase. Moreover the olefin is continuously consumed by the etherification reaction. As a consequence the reaction system converts into only one liquid phase. Now the isobutylene concentration has already decreased to such extend that almost no extra olefinic oligomerization occurs. The absolute olefin concentration might be low, however the olefin concentration is relatively high compared to the olefin concentration in the polar glycerol phase at the start of the reaction. This relatively high olefin concentration results in a rather high etherification reaction rate. The advantages of present invention are that the positive properties of a two phase system at the start of the reaction (low amount of olefin oligomerization by product formation) are combined with the positive properties of a one phase system in the later stage of the reaction (relative high reaction rate). The etherification reactor can be operated batch wise or continuously. If using a batch reactor the two liquid phase system is transferring into an one phase system as function of time. The etherification reaction is a consecutive reaction and can therefore be best executed in a plug flow type reactor. For continuous operation the plug flow behaviour can be approached with several CSTR's in series. Depending on the number of CSTR's in serie, the two liquid phases exist in the first or several first reactors, in the following reactor/s only the one liquid phase can be found.

The reaction mixture from reaction step 1 passes via line 14 to the optional operation units A. Stream 21 comprises mainly the mixture of mono-, di- and tri-alkyl ethers of glycerol, glycerol, isobutylene, water and catalyst. This mixture is neutralized in the next neutralization step 2 by adding organic and/or inorganic bases, such as caustic 22 in a pure form or in a form of water solution for example but not limited to KOH, NaOH, Ca(OH)$_2$, NaHCO$_3$, etc. The salt formed from added caustic and acid catalyst is removed with an appropriate method from the product mixture via line 23. The salts and various impurities possibly present in the processed crude glycerol feed originated from the transesterification process are removed from the system via the neutralization and separation step 2. This operation prevents the salts to build-up in the process via recycle 25. The product flow stream 24 can be fed to additional operation units such as for example a distillation unit where the final glycerol alkyl-ethers 26 are purified from possible low boiling components. The bottom product of the distillation unit consists predominantly of glycerol and mono-alkyl ether of glycerol and can be recycled to the etherification reaction via line 25, or can be separated in an optional down stream separation process and used as such.

The advantage of this process is that the final product is free of olefin oligomers which are not formed in the reaction due to appropriate reaction conditions, an in the olefin phase insoluble homogeneous catalyst and conducting the first period of etherification in separated phases. A second advantage of this process is that because of the salt outlet, glycerol with a certain salt content can be processed in combination with a recycle of mono-alkyl ether and unreacted glycerol. In addition the final reaction product has a low content of mono-ether of glycerol which, when added to the biodiesel, diesel fuel or gasoline, increases the solubility of water in the fuel.

EXAMPLES

The following examples of the reaction step for preparing glycerol alkyl ethers, according to the invention, illustrates the excellent yields of glycerol ethers obtained by varying parameters.

Experimental Setup Description

The experiments were executed in a batch wise operated stirred tank reactor with a total volume of 8 liters. The reactor was equipped with baffles, a jacket, a pressure gauge, a temperature indicator, a drain valve, a funnel, an isobutylene dosing system, an acid dosing system and a pressure relief valve. For the model reactions isobutylene was used as an olefinic hydrocarbon. The isobutylene dosing system consists of an isobutylene gas bottle, a 300 ml gas bomb and interconnecting tubing with manual operated valves. The reactor is heated with aid of a standard thermostatic bath with temperature control. The stirring speed can be manipulated with aid of a frequency converter.

Figure 2:
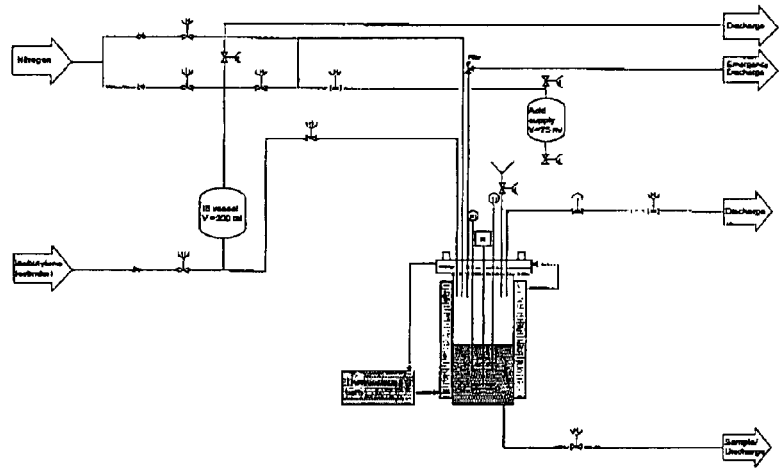
FIG. 2 is a schematic view of one exemplary process for production of glycerol alkyl ethers according to the principles of the present invention.

The scheme is set out in flowsheet FIG. 2.

An experiment was started by adding the requested amount of glycerol into the reactor by using the liquid supply line with funnel. Next, the requested amount of isobutylene (as a liquid) was added by consecutive filling and emptying of the 300 ml gas bomb. Subsequently, the funnel was disconnected and the acid supply connection to the reactor was made. The requested amount of a homogeneous catalyst was dissolved in some glycerol and added to the 75 ml acid supply vessel connected to the hand valve below the funnel. The temperature of the thermostatic bath was set to the requested set point. When the temperature inside the reactor approached the requested set-point the acid/glycerol mixture was supplied into the reactor vessel and the stirrer was switched on. Each experiment continued till a significant drop in pressure was notified (several bars). At the end of each experiment a liquid sample was taken for analysis. A gas chromatograph was used for analysis.

GTBE Results

| Example | No. 1 |
|---|---|
| Temperature | 80° C. |
| Start ratio Isobutylene:Glycerol | 0.5 mol:1 mol |
| Glycerol conversion at equilibrium | 30% |
| Reaction time | 10 hrs |
| Catalyst type | Heterogeneous |
| Catalyst | Amberlyst 15 dry |
| Catalyst concentration | 5 wt % on start amount of glycerol |

| Equilibrium composition | [wt %] |
|---|---|
| Tri-Ether | 2.47E−02 |
| Di-Ether | 4.8 |
| Mono-Ether | 42.9 |
| TBA | Not measured |
| Glycerol | 47.8 |
| Trimethylpentene | 1.0 |
| Isobutylene | 3.5 |
| Water | Not measured |
| Total | 100.0 |

| Example | No. 2 |
|---|---|
| Temperature | 60° C. |
| Start ratio Isobutylene:Glycerol | 2 mol:1 mol |
| Glycerol conversion at equilibrium | 94% |
| Reaction time | 7 hrs |
| Catalyst type | Heterogeneous |
| Catalyst | Amberlyst 15 dry |
| Catalyst concentration | 5 wt % on start amount of glycerol |

| Equilibrium composition | [wt %] |
|---|---|
| Tri-Ether | 2.8 |
| Di-Ether | 46.4 |
| Mono-Ether | 32.7 |
| TBA | Not measured |
| Glycerol | 2.9 |
| Trimethylpentene | 9.1 |
| Isobutylene | 6.1 |
| Water | Not measured |
| Total | 100.0 |

| Example | No. 3 |
|---|---|
| Temperature | 60° C. |
| Start ratio Isobutylene:Glycerol | 5 mol:1 mol |
| Glycerol conversion at equilibrium | 100% |
| Reaction time | 7 hrs |
| Catalyst type | Heterogeneous |
| Catalyst | Amberlyst 36 dry |
| Catalyst concentration | 5 wt % on start amount of glycerol |

| Equilibrium composition | [wt %] |
|---|---|
| Tri-Ether | 13.1 |
| Di-Ether | 37.0 |
| Mono-Ether | 5.3 |
| TBA | Not measured |
| Glycerol | 0.1 |
| Trimethylpentene | 35.5 |
| Isobutylene | 9.0 |
| Water | Not measured |
| Total | 100.0 |

| Example | No. 4 |
|---|---|
| Temperature | 80° C. |
| Start ratio Isobutylene:Glycerol | 0.5 mol:1 mol |
| Glycerol conversion at equilibrium | 33% |
| Reaction time | 7 hrs |
| Catalyst type | Homogeneous |
| Catalyst | Sulfuric acid |
| Catalyst concentration | 1 wt % on start amount of glycerol |

| Equilibrium composition | [wt %] |
|---|---|
| Tri-Ether | 4.11E−02 |
| Di-Ether | 4.4 |
| Mono-Ether | 37.4 |
| TBA | Not measured |
| Glycerol | 51.4 |
| Trimethylpentene | 1.1 |
| Isobutylene | 5.6 |
| Water | Not measured |
| Total | 100.0 |

| Example | No. 9 |
|---|---|
| Temperature | 100° C. |
| Start ratio Isobutylene:Glycerol | 5 mol:1 mol |
| Glycerol conversion at equilibrium | 99% |
| Reaction time | 7 hrs |
| Catalyst type | Heterogeneous |

-continued

| | |
|---|---|
| Catalyst | Amberlyst 35 dry |
| Catalyst concentration | 5 wt % on start amount of glycerol |

| Equilibrium composition | [wt %] |
|---|---|
| Tri-Ether | 16.0 |
| Di-Ether | 31.4 |
| Mono-Ether | 6.3 |
| TBA | Not measured |
| Glycerol | 0.3 |
| Trimethylpentene | 26.6 |
| Isobutylene | 17.4 |
| Water | Not measured |
| Total | 100.0 |

| | |
|---|---|
| Example | No. 10 |
| Temperature | 68° C. |
| Start ratio Isobutylene:Glycerol | 2 mol:1 mol |
| Glycerol conversion at equilibrium | 100% |
| Reaction time | 7 hrs |
| Catalyst type | Heterogeneous |
| Catalyst | Amberlyst 35 dry |
| Catalyst concentration | 5 wt % on start amount of glycerol |

| Equilibrium composition | [wt %] |
|---|---|
| Tri-Ether | 10.7 |
| Di-Ether | 59.5 |
| Mono-Ether | 22.1 |
| TBA | 0.0 |
| Glycerol | 0.0 |
| Trimethylpentene | 4.9 |
| Isobutylene | Not measured |
| Water | 2.8 |
| Total | 100.0 |

| | |
|---|---|
| Example | No. 11 |
| Temperature | 56° C. |
| Start ratio Isobutylene:Glycerol | 2 mol:1 mol |
| Glycerol conversion at equilibrium | 97.2% |
| Reaction time | 10 hrs |
| Catalyst type | Homogeneous |
| Catalyst | Sulfuric acid |
| Catalyst concentration | 0.5 wt % on start amount of glycerol |

| Equilibrium composition | [wt %] |
|---|---|
| Tri-Ether | 14.3 |
| Di-Ether | 58.2 |
| Mono-Ether | 24.7 |
| TBA | 0.0 |
| Glycerol | 1.3 |
| Trimethylpentene | 0.0 |
| Isobutylene | Not measured |
| Water | 1.5 |
| Total | 100.0 |

| | |
|---|---|
| Example | No. 12 |
| Temperature | 65° C. |
| Start ratio Isobutylene:Glycerol | 4 mol:1 mol |
| Glycerol conversion at equilibrium | 100% |
| Reaction time | 12 hrs |
| Catalyst type | Homogeneous |
| Catalyst | Sulfuric acid |
| Catalyst concentration | 1 wt % on start amount of glycerol |

-continued

| Equilibrium composition | [wt %] |
|---|---|
| Tri-Ether | 24.3 |
| Di-Ether | 62.7 |
| Mono-Ether | 9.8 |
| TBA | 0.9 |
| Glycerol | 0.0 |
| Trimethylpentene | 0.2 |
| Isobutylene | Not measured |
| Water | 2.1 |
| Total | 100.0 |

| | |
|---|---|
| Example | No. 5 |
| Temperature | 80° C. |
| Start ratio Isobutylene:Glycerol | 2 mol:1 mol |
| Glycerol conversion at equilibrium | 90% |
| Reaction time | 7 hrs |
| Catalyst type | Heterogeneous |
| Catalyst | Amberlyst 35 dry |
| Catalyst concentration | 5 wt % on start amount of glycerol |

| Equilibrium composition | [wt %] |
|---|---|
| Tri-Ether | 3.6 |
| Di-Ether | 40.8 |
| Mono-Ether | 33.6 |
| TBA | Not measured |
| Glycerol | 4.5 |
| Trimethylpentene | 8.2 |
| Isobutylene | 9.3 |
| Water | Not measured |
| Total | 100.0 |

| | |
|---|---|
| Example | No. 6 |
| Temperature | 80° C. |
| Start ratio Isobutylene:Glycerol | 5 mol:1 mol |
| Glycerol conversion at equilibrium | 99% |
| Reaction time | 7 hrs |
| Catalyst type | Heterogeneous |
| Catalyst | Amberlyst 35 dry |
| Catalyst concentration | 5 wt % on start amount of glycerol |

| Equilibrium composition | [wt %] |
|---|---|
| Tri-Ether | 15.2 |
| Di-Ether | 34.0 |
| Mono-Ether | 5.7 |
| TBA | Not measured |
| Glycerol | 0.2 |
| Trimethylpentene | 31.3 |
| Isobutylene | 13.0 |
| Water | Not measured |
| Total | 100.0 |

| | |
|---|---|
| Example | No. 7 |
| Temperature | 100° C. |
| Start ratio Isobutylene:Glycerol | 0.5 mol:1 mol |
| Glycerol conversion at equilibrium | 27% |
| Reaction time | 7 hrs |
| Catalyst type | Heterogeneous |
| Catalyst | Amberlyst 15 dry |
| Catalyst concentration | 5 wt % on start amount of glycerol |

| Equilibrium composition | [wt %] |
|---|---|
| Tri-Ether | 5.10E−02 |
| Di-Ether | 3.6 |

-continued

| | |
|---|---|
| Mono-Ether | 31.2 |
| TBA | Not measured |
| Glycerol | 55.7 |
| Trimethylpentene | 1.1 |
| Isobutylene | 8.4 |
| Water | Not measured |
| Total | 100.0 |

| | |
|---|---|
| Example | No. 8 |
| Temperature | 100° C. |
| Start ratio Isobutylene:Glycerol | 2 mol:1 mol |
| Glycerol conversion at equilibrium | 84% |
| Reaction time | 7 hrs |
| Catalyst type | Homogeneous |
| Catalyst | Sulfuric acid |
| Catalyst concentration | 1 wt % on start amount of glycerol |

| Equilibrium composition | [wt %] |
|---|---|
| Tri-Ether | 3.9 |
| Di-Ether | 33.9 |
| Mono-Ether | 34.3 |
| TBA | Not measured |
| Glycerol | 7.1 |
| Trimethylpentene | 7.2 |
| Isobutylene | 13.6 |
| Water | Not measured |
| Total | 100.0 |

| | |
|---|---|
| Example | No. 13 |
| Temperature | 78° C. |
| Start ratio Isobutylene:Glycerol | 4 mol:1 mol |
| Glycerol conversion at equilibrium | 100% |
| Reaction time | 13 hrs |
| Catalyst type | Homogeneous |
| Catalyst | Sulfuric acid |
| Catalyst concentration | 1 wt % on start amount of glycerol |

| Equilibrium composition | [wt %] |
|---|---|
| Tri-Ether | 26.1 |
| Di-Ether | 59.7 |
| Mono-Ether | 9.1 |
| TBA | 0.5 |
| Glycerol | 0.0 |
| Trimethylpentene | 0.2 |
| Isobutylene | Not measured |
| Water | 4.3 |
| Total | 100.0 |

| | |
|---|---|
| Example | No. 14 |
| Temperature | 60° C. |
| Start ratio TBA:Glycerol | 5 mol:1 mol |
| Glycerol conversion at equilibrium | 74% |
| Reaction time | 10 hrs |
| Catalyst type | Homogeneous |
| Catalyst | Sulfuric acid |
| Catalyst concentration | 1 wt % on start amount of glycerol |

| Equilibrium composition | [wt %] |
|---|---|
| Tri-Ether | 1.32E−01 |
| Di-Ether | 7.7 |
| Mono-Ether | 18.1 |
| TBA | 53.3 |
| Glycerol | 5.3 |
| Trimethylpentene | 0.6 |
| Isobutylene | 1.4 |
| Water | 3.5 |
| Total | 100.0 |

| | |
|---|---|
| Example | No. 15 |
| Temperature | 80° C. |
| Start ratio TBA:Glycerol | 2 mol:1 mol |
| Glycerol conversion at equilibrium | 44% |
| Reaction time | 8 hrs |
| Catalyst type | Heterogeneous |
| Catalyst | Amberlyst 15 dry |
| Catalyst concentration | 5 wt % on start amount of glycerol |

| Equilibrium composition | [wt %] |
|---|---|
| Tri-Ether | 5.77E−02 |
| Di-Ether | 4.4 |
| Mono-Ether | 24.2 |
| TBA | 42.7 |
| Glycerol | 21.4 |
| Trimethylpentene | 0.5 |
| Isobutylene | 2.4 |
| Water | 4.3 |
| Total | 100.0 |

| | |
|---|---|
| Example | No. 16 |
| Temperature | 100° C. |
| Start ratio TBA:Glycerol | 0.5 mol:1 mol |
| Glycerol conversion at equilibrium | 13% |
| Reaction time | 9 hrs |
| Catalyst type | Homogeneous |
| Catalyst | Sulfuric acid |
| Catalyst concentration | 1 wt % on start amount of glycerol |

| Equilibrium composition | [wt %] |
|---|---|
| Tri-Ether | 3.74E−03 |
| Di-Ether | 0.7 |
| Mono-Ether | 14.1 |
| TBA | 16.5 |
| Glycerol | 62.3 |
| Trimethylpentene | 0.2 |
| Isobutylene | 3.3 |
| Water | 2.9 |
| Total | 100.0 |

The invention claimed is:

1. A process for the production of glycerol alkyl ethers by glycerol etherification with straight, branched or cyclic olefinic hydrocarbons having 2 to 10 carbon atoms, and/or the corresponding aldehydes, ketones and alcohols, in the presence of homogeneous acid catalyst, comprising a reaction step, wherein a first period of the reaction operates in a multi phase system comprising a polar glycerol phase comprising mainly glycerol and the homogenous acid catalyst, and a non-polar hydrocarbon phase comprising mainly olefinic hydrocarbons having 2 to 10 carbon atoms, and/or the corresponding aldehydes, ketones and alcohols wherein the first period results in the lowering of polarity, and wherein a second period of the reaction operates in a single reaction phase due in part to the lowering of polarity in the first period of the reaction, so that the formation of olefin oligomers is hindered; and a step for the neutralization of the acid catalyst and separation of formed salt.

2. The process of claim 1, wherein the reaction step comprises a reactor system, wherein partly two distinct reaction phases are present, wherein in the first period of the reaction, olefin, and/or the corresponding aldehydes, ketones and alcohols, oligomerization by-product formation is prevented by the combination of two separate liquid phases, including a hydrocarbon phase and a glycerol phase, and the choice of a homogeneous catalyst, which is insoluble in the olefin phase, and wherein in the second period of the reaction, when the concentration of ethers is increased and the concentration of olefin is decreased, only one phase is observed, in which the etherification reaction rate is relatively high.

3. The process of claim 1, comprising a recycle of the glycerol and/or mono-ether.

4. The process according to claim 1, wherein the reaction is carried out in a continuous manner or batch manner.

5. The process according to claim 4, wherein the continuous reaction is carried out in a plug flow reactor (PFR) or a cascade of continuous stirred tank reactors (CSTR).

6. The process according to claim 1, wherein the operating temperature is in the range of 40 to 180° C., and the process pressure is in the range of 1 atm to 100 atm.

7. The process according to claim 1, wherein treated or untreated glycerol, which contains a certain salt level, is used.

8. The process according to claim 1, wherein a homogeneous acid catalyst is used and is soluble in the glycerol phase and substantially insoluble in the hydrocarbon phase, and is selected from the group comprising sulfuric acid, p-toluenesulfonic acid, and methanesulfonic acid.

9. The process according to claim 1, wherein an acid catalyst is used, and the amount of the acid catalyst is in the range of 0.1 to 10 wt %.

10. The process according to claim 1, wherein the olefinic hydrocarbon having 2 to 10 carbon atoms, and/or the corresponding aldehydes, ketones and alcohols, and/or glycerol is applied in a mole ratio range of 0.1:1 to 10:1.

11. The process according to claim 1, wherein the olefinic hydrocarbon is isobutylene.

12. The process according to claim 1, wherein an inorganic base or an organic base is used for neutralization of an acid catalyst.

13. The process according to claim 1 for the production of glycerol alkyl ethers by the reaction of glycerol with straight, branched, or cyclic olefins and/or the corresponding aldehydes, ketones and alcohols having from 2 to 10 carbon atoms, wherein the process includes the steps of creating a two-phase system, the first phase being a polar glycerol phase including a homogeneous acid catalyst, and a non-polar olefin phase comprising or including the chosen olefin, and/or the corresponding aldehydes, ketones and alcohols the reaction conditions favouring the reaction between the glycerol and olefin and/or the corresponding aldehydes, ketones and alcohols over the oligomerisation of the olefin, and/or the corresponding aldehydes, ketones and alcohols allowing the process to proceed, neutralizing the polar phase and recovering the resulting glyceryl ether.

14. The process according to claim 1, wherein the glycerol phase is derived from a transesterification process.

15. The process according to claim 1, wherein the operating temperature is in the range of 60 to 90° C., and the process pressure is in the range of 3 atm to 50 atm.

16. The process according to claim 1, wherein an acid catalyst is used, and the amount of the acid catalyst is in the range of 0.5 to 6 wt %.

17. The process according to claim 1, wherein KOH is used for neutralization of an acid catalyst.

18. The process of claim 2, comprising a recycle of the glycerol and/or mono-ether.

19. The process according to claim 2, wherein the reaction is carried out in a continuous manner or batch manner.

20. The process according to claim 3, wherein the reaction is carried out in a continuous manner or batch manner.

* * * * *